United States Patent [19]

Pieters et al.

[11] 4,226,812
[45] Oct. 7, 1980

[54] PROCESS FOR PRODUCING CHLOROTRIFLUOROETHYLENE

[75] Inventors: Wim J. M. Pieters, Morristown; William E. Gates, Andover; Franz Wenger, Mountainside, all of N.J.

[73] Assignee: Allied Chemical Corporation, Morris Township, Morris County, N.J.

[21] Appl. No.: 854,919

[22] Filed: Nov. 25, 1977

[51] Int. Cl.³ .................. C07C 21/18; C07C 19/045; C07C 21/06; B01J 27/00
[52] U.S. Cl. .................. 570/157; 252/441; 570/247
[58] Field of Search ............ 252/441; 260/653.4, 260/653.5, 656 R, 659 A

[56] References Cited

U.S. PATENT DOCUMENTS

| | | | |
|---|---|---|---|
| 2,697,124 | 12/1954 | Mantell | 260/453 |
| 3,210,431 | 10/1965 | Engel | 260/659 |
| 3,332,885 | 7/1967 | Imoto et al. | 252/441 |
| 3,333,011 | 7/1967 | Anello et al. | 260/653.5 |
| 3,579,597 | 5/1971 | Antonini et al. | 252/441 |
| 3,721,632 | 3/1973 | Miller et al. | 252/441 |
| 3,926,847 | 12/1975 | Beard, Jr. et al. | 252/441 |
| 4,039,596 | 8/1977 | Pieters et al. | 260/653.7 |

OTHER PUBLICATIONS

Chemical Physics Letters–98, pp. 1353–1363, Rabo et al.

Journal Chemical Society–1958, pp. 299–304, Barrer and Meier.

Inorganic Chem., 9 No. 6, 1970, pp. 1330–1333, Liquornik and Irvine.

Journal Org. Chem., vol. 36, 1971, pp. 3651–3653, Moore and Henry.

*Primary Examiner*—P. E. Konopka
*Attorney, Agent, or Firm*—Robert A. Harman

[57] ABSTRACT

An improved process is described for producing chlorotrifluoroethylene, a useful monomer for making high strength chlorofluoropolymers, comprising passing a mixture of 1,1,2-trichloro-1,2,2-trifluoroethane, ethylene, hydrogen chloride and elemental oxygen in the vapor phase, at a temperature from about 350° to 525° C., over a catalyst consisting essentially of a mixture of copper chloride and an alkali metal chloride, preferably a eutectic mixture, occluded in a molecular sieve, having an average pore size diameter in the range of about 5 to 11 angstroms.

A new catalyst composition is also described, useful in oxyhydrochlorination processes conducted at temperatures above 350° C., consisting essentially of a mixture of copper chloride and an alkali metal chloride, preferably a eutectic mixture, occluded in a molecular sieve, having an average pore size diameter in the range of about 5 to 11 angstroms.

11 Claims, No Drawings

PROCESS FOR PRODUCING CHLOROTRIFLUOROETHYLENE

BACKGROUND OF THE INVENTION

1. Field of the Invention

This invention relates to an improved process for producing chlorotrifluoroethylene, a useful monomer, involving the dechlorination of 1,1,2-trichloro-1,2,2-trifluoroethane at temperatures above 350° C. in the presence of a molecular sieve/copper chloride-alkali metal chloride catalyst.

2. Brief Description of the Prior Art

Polychlorotrifluoroethylene (PCTFE) is a very useful polymer and is employed in the production of thermoplastic copolymers having high impact strength, high solvent resistance and low moisture absorption. The copolymers are utilized in the making of a wide variety of useful industrial articles including chemical piping, gaskets, tank linings, connectors, insulation materials and electronic components.

Since the demand for the polymer is ever increasing, new processes for producing the monomer, chlorotrifluoroethylene (CTFE) are constantly being searched for.

Some commercial processes for producing CTFE involve the dechlorination of 1,1,2-trichloro-1,2,2-trifluoroethane (TCTFE), by using sodium amalgam or zinc dust in alcohol. However, these and other prior art processes employing similar types of dehalogenation reagents, require the use of either dangerous or expensive metal reagents and spent liquors from such processes pose inherent pollution problems.

Two prior art references, U.S. Pat. No. 2,697,124 (1954) and U.S. Pat. No. 3,333,011 (1967, Allied Chemical) describe processes involving dechlorination of 1,1,2-trichloro-1,2,2-trifluoroethane using hydrogen gas. However, these processes possess the disadvantages of requiring a combustible gas, with its attendant hazards, for use in large scale industrial processes for the production of CTFE.

U.S. Pat. No. 2,697,124 (1954) describes a process for dehalogenating fluorochlorocarbons, in the presence of a hydrogen supplying compound, such as ethylene, and a solid catalyst at a temperature of about 100° to about 800° C. Although the process discloses the dechlorination of TCTFE to CTFE, no mention is made of a molecular sieve/copper chloride-alkali metal chloride type of catalyst.

U.S. Pat. No. 3,210,431 (1965) is a related process wherein ethylene is converted to ethylene dichloride by an oxyhydrochlorination reaction. A mixture of ethylene, hydrogen chloride and oxygen is passed over a catalyst comprising copper chloride, didymium chloride, alkali metal chloride and a silica gel carrier at a temperature of about 100° to 300° C. However, the catalyst is not described as being useful at temperatures above 350° C. We have found that normal Deacon-type catalysts do not exhibit a sustained catalyst lifetime in the catalyzed vapor-phase reaction between TCTFE and ethylene in the presence of hydrogen chloride and elemental oxygen at temperatures above 350° C.

U.S. Pat. No. 4,039,596 (1977, Allied Chemical) describes a process for oxyhydrochlorination of C—H containing organic compounds, including methane and ethylene, in the presence of a copper-calcium fluoride catalyst. However, no suggestion is made regarding the utility of the catalyst for dechlorinating compounds such as chlorinated paraffinic hydrocarbons at temperatures above 350° C.

Zeolite-salt occlusion type catalysts are known in the art and representative examples are described in *Chem. Phys. Letters*, 98,1353–63 (Rabo et al.); *J. Chem. Soc.* 1958, pp. 299–304 (Barrer and Meier); and *Inorg. Chem.* 9, No. 6, pp. 1330–1333 (1970, Liquornik and Irvine). However the above references do not discuss or suggest the possibility of forming occlusion complexes of zeolite/copper chloride-alkali metal chloride mixtures for use as catalysts in oxyhydrochlorination processes.

It is known that organic chlorine compounds can be formed from a Deacon-type process, wherein hydrogen chloride is reacted with oxygen to produce chlorine gas in the presence of a catalyst. The in situ formed chlorine is allowed to react with an organic compound such as methane or ethylene to produce a chlorinated product either by a substitution or addition type reaction.

It is also known that organic chlorofluorocarbons can be dechlorinated in the presence of a catalyst by use of an organic chlorine acceptor. The reference, *J. Org. Chem.*, Vol. 36, pp. 3651–53 (1971), describes the use of CTFE as a chlorine acceptor in the dechlorination of $CFCl_2$—$CFCl_2$. However, the reference describes ethylene as being a relatively poor "chlorine sink" in such a chlorine-exchange reaction.

Fellow colleagues of the inventors herein, and having the same assignee, have shown that TCTFE can be dechlorinated to CTFE in the presence of ethylene, by virtue of the fact that chlorine will add to the double bond of ethylene producing ethylene dichloride, EDC. However, in general, the reaction temperature required is usually above 350° C. for good results and the reductive elimination of chlorine from the chlorinated organic compound usually causes carbonaceous products on the catalyst surface which results in reduced catalyst effectiveness.

A very effective catalyst used in the Deacon process is a cupric chloride/potassium chloride eutectic mixture usually used in a form supported on an inert, high surface area substrate such as silica, alumina, titanium and the like. However, at temperatures above 350° C., the active phase of the catalyst will sublime, thus causing a significant decrease in catalyst activity.

We have discovered that a catalyst consisting essentially of an occlusion complex of zeolite/copper chloride-alkali metal chloride eutectic mixture is an effective catalyst at temperatures above 350° C., for dechlorinating 1,1,2-trichloro-1,1,2-trifluoroethane to produce chlorotrifluoroethylene in the presence of ethylene, hydrogen chloride and elemental oxygen, also producing ethylene dichloride as a by-product.

SUMMARY

In accordance with this invention, there is provided an improved process for converting 1,1,2-trichloro-1,2,2-trifluoroethane to chlorotrifluoroethylene, the improvement which comprises passing said trichlorotrifluoroethane in a mixture of oxygen, hydrogen chloride and ethylene in the vapor phase over a catalyst consisting essentially of a mixture of copper chloride and an alkali metal chloride occluded in a molecular sieve, having an average pore size diameter in the range of about 5 to 11 angstroms, at a temperature in the range of about 350° C. to 525° C., for a contact time of about 0.1 to 30 seconds.

Also provided is a catalyst composition consisting essentially of a mixture of copper chloride and an alkali metal chloride occluded in a molecular sieve having an average pore size diameter in the range of about 5 to 11 angstroms.

DESCRIPTION OF THE INVENTION AND PREFERRED EMBODIMENTS

The present invention provides a novel process for dechlorinating 1,1,2-trichloro-1,2,2-trifluoroethane (TCTFE) to form chlorotrifluoroethylene (CTFE) under oxyhydrochlorination conditions, using ethylene as a chlorine acceptor, at temperatures above 350° C.

The novelty of the process is in conducting the dechlorination of TCTFE, under oxyhydrochlorination conditions, at temperatures above 350° C., in the presence of a catalyst that exhibits effective catalyst lifetimes under the conditions employed. Preferably, the catalyst is a eutectic mixture, and by the term "eutectic mixture" is meant a solid solution of two or more components in particular proportions, wherein the mixture possesses a melting point, usually below the melting point of all the component constituents. By virtue of the fact that the catalyst mixture is occluded inside of the porous cage-structure of the molecular sieve, a large surface area of the catalyst is obtained. If the catalyst mixture is a liquid eutectic mixture, it is constrained from flowing out of the porous cavities of the molecular sieve at high temperatures. The occlusion of the copper chloride adduct in the cage provided by the molecular sieve is irreversible in the sense as discussed in the above-cited article, Chem. Phys. Letters 98, p. 1353. No sublimation of copper chloride is detectable at temperatures below about 700° C. In contrast to conventional copper chloride/alkali metal halide catalysts, wherein the eutectic mixture is simply supported on the surface of the substrate, and is mobile and volatile, this new type of catalyst composition can be used in processes involving Deacon-type reactions and reductive elimination of chlorine, at temperatures above 350° C., without significant reduction in the catalyst activity, due to agglomeration or to loss of the eutectic mixture through sublimation.

A preferred class of molecular sieves for use in the process are the zeolites, crystalline metal aluminosilicates which may also contain sodium, potassium and calcium metal cations. By the term "molecular sieve", a term well known in the catalyst art, is meant a crystalline cage-like aluminosilicate solid having a porous surface and a three-dimensional interconnecting cage network structure of silica and alumina tetrahedra. Conventional zeolites are classified either as A, X or Y-types wherein the A-type refers to a small average pore size diameter from about 3 to 5 angstroms, and X and Y-types refer to an average pore size diameter of about 9 to 11 angstroms. Preferred zeolites for use in this invention are those of the X and Y-types, containing sodium ion, wherein the average pore size diameter is about 5 to 11 angstroms and a preferred pore size is about 10 angstroms corresponding to a conventional zeolite classified as "13 X". Pore size diameters of less than 5 angstroms lead to large amounts of combustion products from ethylene in the process and thus are not desirable.

The copper chloride-alkali metal chloride portion of the invention catalyst can be prepared in basically two ways. One way is to use a mixture of chlorides, i.e. copper chloride and alkali metal chloride, in the form of a melt and then fuse the molten mixture with the molecular sieve to be used. The other way is to use a mixture of non-chlorides, such as copper sulfate, and an alkali metal salt, such as potassium bromide, forming a melt of the two compounds, and fusing the resulting melt with the molecular sieve to be used. The melt occluded into the molecular sieve cage structure will be subsequently converted to a copper chloride-alkali metal chloride mixture upon contact with hydrogen chloride in the process, thus forming the catalyst of the invention. Thus, the anions of the starting copper and alkali metal salts are immaterial, since they will be replaced by chlorine from hydrogen chloride during the process to form the active catalyst. The only requirement of the salts is that the mixture thereof should form a melt below 400° C., prior to fusion with the molecular sieve, this being necessary since at about 400° C., the molecular sieve starts to undergo thermal decomposition.

In general, the fusion steps are carried out under a nitrogen atmosphere by initial fusion at about 400° C., followed by heating at temperatures of about 500° C. for periods of several hours. The obtained fused solid may then optionally be washed with water to remove any unoccluded halide salt, followed by calcining, or may be used directly in the process as is.

Copper chloride is usually employed as copper (II) chloride, but can also be present as copper (I) chloride, or mixtures of both. Preferably, the anhydrous forms of copper chloride are used.

The alkali metal chloride can contain any metallic cation selected from Group I in the periodic table and includes lithium, sodium, potassium, rubidium, cesium and francium. Generally, potassium is a preferred metal cation.

Copper and alkali metal salts may contain fluoride, chloride, bromide, iodide, sulfate anions and the like in the preparation of the catalyst prior to contacting with hydrogen chloride. A preferred anion for both copper and alkali metal salts is chloride.

In general, the molar ratio of copper chloride/alkali metal chloride salt employed in this invention is about 1:1, whereby the eutectic mixture is obtained, and slightly greater or smaller molar ratios with respect to the copper chloride can be used with like results. The weight ratio of molecular sieve/copper chloride-alkali metal chloride mixture in the catalyst is usually about 6 parts molecular sieve to 4 parts mixture by weight and slightly greater or smaller ratios of the copper chloride-alkali metal chloride mixture with respect to the molecular sieve can be used.

In addition, the invention catalyst may contain small amounts of rare earth chlorides, in the lanthanum family of the periodic table, for example, lanthanum chloride, neodymium chloride, praseodymium chloride, samarium chloride and the like. Mixtures of the lanthanide chlorides can also be employed, for example, a mixture of the above recited chlorides, prepared from a mixture of the above rare earth metals, referred to as "didymium". In such eutectic mixtures, the molar ratio of copper chloride/alkali metal chloride/rare earth chloride is about 7:4:1. As discussed above, fluorides, chlorides, bromides, iodides, sulfates and the like, of the rare earth metals can be used, and preferably chlorides to initially prepare the copper alkali metal salt mixtures before contacting with hydrogen chloride in the process.

A preferred eutectic mixture, copper chloride/potassium chloride, in a 1:1 molar ratio, has a melting point of about 350° C. and is a very effective catalyst in the process.

It is also to be understood that different proportions of the catalyst components from those characterizing the eutectic mixtures are operative for purposes of this invention but have the disadvantage of having a higher melting range which may make the desired occlusion more difficult.

In general, the particle size of the catalyst depends upon the apparatus and conditions employed. In small scale fixed bed reactors, a particle size of about 60 to 100 mesh can be used. For fluidized beds, powders can be used and in moving beds, pellets of ⅛" in size can be effectively employed.

The catalyst does not require special techniques of activation prior to use.

The basic part of the reaction process is the dechlorination of TCTFE with ethylene, in the presence of the novel catalyst of this invention, to form CTFE as the main product and VCM and EDC as coproducts. Generally, small amounts of HCl will be formed in the process, and advantage can be taken of this fact by conducting the process under oxyhydrochlorination conditions wherein quantities of oxygen gas are introduced to oxidize the HCl to free chlorine which can then react with additional ethylene to form EDC. The added oxygen also serves to prevent the formation of carbonaceous materials on the catalyst surface, thus preserving catalyst lifetime. A minimum amount of HCl is required in the reaction zone to maintain the catalyst in the active chloride form. The process can be conducted by utilizing small or large amounts of HCl, O₂ and ethylene as starting materials, depending upon the amount of VCM and EDC desired in the process.

If small quantities of VCM and EDC are desired, then it is preferred to use a minimum amount of ethylene, equal to the amount of chlorine produced from the dechlorination of TCTFE and that produced from the oxidation of byproduct HCl produced in the process. Here, little or no HCl is introduced in the inlet stream, the catalyst activity being maintained by the small amount of HCl formed in situ, and an amount of O₂ is introduced sufficient to just oxidize the HCl formed in situ.

If larger amounts of VCM and EDC are desired, then progressively larger amounts of ethylene, O₂ and HCl in relation to TCTFE are utilized in the inlet feed stream. Thus, the overall process can be varied with respect to the amount of VCM and EDC coproducts formed.

In one preferred embodiment, two moles of EDC are formed per mole of CTFE.

This preferred embodiment of the invention process can be represented by the following equation:

$$2HCl + \tfrac{1}{2} O_2 + 2C_2H_4 + CF_2ClC-CFCl_2 \longrightarrow$$
$$\text{ethylene} \qquad \text{TCTFE}$$
$$2C_2H_4Cl_2 + CF_2=CFCl + H_2O$$
$$\text{EDC} \qquad \text{CTFE}$$

The overall stoichiometry of the process is continuously adjusted during the course of the reaction in relation to the concentration of TCTFE in the inlet, which is fed as a saturated nitrogen stream.

Individual processes that occur during the overall process include those represented by the following equations:

$$\tfrac{1}{2} O_2 + 2HCl \longrightarrow Cl_2 + H_2O \qquad (1)$$

$$Cl_2 + C_2H_4 \longrightarrow C_2H_4Cl_2 \qquad (2)$$
$$\quad \text{ethylene} \quad\;\; \text{EDC}$$

$$CF_2Cl-CFCl_2 + C_2H_4 \longrightarrow CF_2=CFCl + C_2H_4Cl_2 \qquad (3)$$
$$\text{TCTFE} \quad\;\; \text{ethylene} \quad\;\; \text{CTFE} \quad\;\; \text{EDC}$$

$$C_2H_4 + 2O_2 \longrightarrow 2CO + 2H_2O \qquad (4)$$
$$\text{ethylene}$$

$$2CO + O_2 \longrightarrow 2CO_2 \qquad (5)$$

$$C_2H_4Cl_2 \longrightarrow CH_2=CHCl + HCl \qquad (6)$$
$$\text{EDC} \qquad\quad \text{VCM}$$

Equations 1, 2 and 3 represent the main desired reactions of the process and equations 4, 5 and 6 represent accompanying side reactions. Equations 4 and 5 represent loss of ethylene in the reaction due to combustion processes, which normally total only about 5% of the ethylene converted. The conversion of EDC to VCM in equation 6 represents dehydrochlorination of EDC to form VCM which is vinylchloride monomer. Thus, EDC which is normally used to prepare VCM, can be utilized in the reaction to directly prepare the VCM monomer in the process as a valuable by-product. This can be accomplished in high yield, for example, by separating out EDC and VCM from the product stream, and passing the materials through a separate column to thermally convert EDC to VCM.

Processes represented by equations (1), (3), (4) and (5) are catalyst-promoted in the overall process. Processes represented by equations (2) and (6) are known to proceed thermally, but are probably assisted in the overall process in the presence of the catalyst.

In general, any conventional type of reactor or reaction zone apparatus may be employed, to effect the dechlorination of TCTFE, which is resistant to hydrogen chloride and includes reactors made from quartz, Inconel, a corrosion-resistant nickel type of metal alloy, high grade steel, fused alumina refractory and the like.

In general, the process includes the steps of: preparing the catalyst; placing the catalyst into the reactor; optionally, activating the catalyst; and passing feed streams of the gases, monitored at known concentrations through the reactor, preferably by using electronic flow controllers, for known calculated contact times; analyzing the exit streams by gas chromatography versus known concentrations of standards, optionally with the aid of a programmed computer in series with the chromatographic analysis. Variations and modifications of the apparatus and process including the analysis of the product streams by an automated system will be obvious to one skilled in the art.

In general, an amount of ethylene relative to TCTFE of up to about 2 to 1 moles of ethylene per mole of TCTFE can be used, the minimum amount being that equivalent to the amount of TCTFE converted; an amount of HCl relative to ethylene of up to about 1 mole HCl per mole ethylene can be used, the minimum amount being that sufficient to maintain the catalyst in the active form; and an amount of HCl relative to O₂ of up to about 4 moles of HCl per mole of O₂ can generally be used. One preferred process utilizes a molar ratio of TCTFE/ethylene/HCl/O₂ of about 2:4:4:1.

The desired amount of fresh HCl charge in the inlet feed can be reduced or eliminated by recycling the HCl resulting from the thermal dehydrochlorination of EDC at the end of the process.

The process is usually conducted in the temperature range from about 350° to 525° C. and preferably from about 450° to 500° C. Particularly preferred is a process temperature of about 475° C.

Contact times of about 0.1 to 30 seconds can be employed and it is preferred to use contact times of about 1 to 3 seconds. Contact time as used herein is defined as catalyst void space (taken as 50% of bed volume) divided by inlet gas flow rate at reaction temperature.

Percent conversion of TCTFE in the process is generally about 1 to 10 percent based on the amount of TCTFE employed.

Since TCTFE does not undergo combustion in the process, it is assumed that the amount of TCTFE converted results in a quantitative yield of CTFE, with lower yields of CTFE being the result of errors in measurement or losses in handling.

Percent conversion of ethylene in the process is generally about 30 to 60% based on the amount of ethylene employed in the process. Yields of ethylene dichloride, EDC, based on the amount of ethylene conversion, are generally in the range of about 70 to 95% of theory. Percent ethylene consumed by combustion is usually about 3 to 10% and preferably not over 5%.

Because of the high selectivity of the process in dechlorinating TCTFE, without any accompanying defluorination occurring, higher overall conversions can be accomplished by a recycle of the product stream in successive passes through the reactor or apparatus employed.

The following examples illustrate the best mode of carrying out the invention, as contemplated by us, but should not be construed as being limitations on the scope and spirit of the instant invention.

EXAMPLE A

Preparation of Catalyst

Ten grams of a 5X molecular sieve having an average pore size diameter of about 5 angstroms was heated at about 250° C. for about 2 hours under vacuum.

A mixture of 4.3 grams anhydrous cupric chloride and 2.4 grams potassium chloride was heated to form a eutectic melt under a low natural gas flame just above the eutectic melting point under a nitrogen atmosphere for about 20 minutes. The resulting melt was cooled to solidify and then ground and sized through a 20 mesh screen.

The fused copper chloride/potassium chloride eutectic powder was then thoroughly mixed with the molecular sieve and the mixture fused under a nitrogen atmosphere at a temperature about 300° C. for about 20 minutes. The temperature was then raised to about 400° C. and the fused material was heated for about 20 minutes. The fused material was cooled and washed with water to remove free copper, potassium and chloride ions. The material was then dried at 200° C. for about one day under a nitrogen atmosphere. The obtained material was then directly used in the oxyhydrochlorination process, described in Example D.

EXAMPLE B

Preparation of Catalyst (1180)

Essentially the same procedure was used for preparation of the catalyst as described above in Example A except that a molecular sieve of type 13X, having an average pore size diameter of about 10 angstroms was used, and the fused material was not washed with water, following the fusion step, but was used directly as is.

DESCRIPTION OF THE PROCEDURE

The catalysts prepared in Examples A and B were tested in oxyhydrochlorination runs with ethylene and TCTFE.

The reactor used consisted essentially of an open-ended quartz tube, surrounded by a jacket, and supported in an electrically heated furnace. Reactant gases were supplied through a gas manifold. The individual gases were controlled with Tylan® electronic flow controllers. The jacket was sealed to the inner tube near the top of that tube and closed over below the open bottom end of the reactor tube. The reactant gases entered the jacket through a side arm, flowed down the annulus between the jackets and the inner tube to the closed off bottom portion of the jacket and then rose there into the open end of the reactor tube, passed through the catalyst bed therein and exited from the top of the reactor tube. The exit manifold delivered the reactants to product separating chromatographic columns and associated detectors and vent. The flows of the reactant gases were set and regulated by a electronic flow controllers. TCTFE, was fed as a saturated inlet stream by bubbling nitrogen through a saturator, a vessel containing liquid TCTFE which was fitted with a glass fritted tube. The flow of nitrogen through the liquid created a TCTFE saturated nitrogen stream, whose inlet concentration was also controlled by an electronic flow controller. Total pressure of the combined reactant mixture was recorded by a pressure recorder ahead of the inlet. Use of the electronic flow controllers permitted very precise measurements of the inlet concentrations of each gaseous reactant.

The inlet stream was analyzed after reaching steady state conditions, by selectively separating the stream into different boiling fractions and passing each fraction through a column chromatograph which was connected to a time-sharing computer programmed to analyze the nature and amounts of each constituent in the fraction.

The exit stream was analyzed by the procedure described above, about 30 minutes later, the time required to make the automatic computerized analysis of each sample. Each run described below was conducted in 70 minute intervals.

In the runs, the inlet and outlet concentrations are expressed as volume percent of the total flow concentration. The volumetric flow rates in the outlet are adjusted to a basis of 100 volumes of inlet gas, by multiplying each value by [$N_2$(in)/$N_2$ (out)]. Since the volume percent of each constituent is for practical purposes, approximately equal by proportions to the mol percent of each constituent, the volume percent figures were treated as mol percent figures in the calculations.

EXAMPLE C

The catalyst prepared in Example B was used in a series of 9 runs wherein the catalyst weight used was 4.3016 grams, total catalyst bed volume was 4.5 ml, and the flow rate of the inlet gaseous stream was 39 ml/min (STP). The average contact time in the runs was about 1.3 seconds. Nitrogen was used to normalize the inlet and outlet concentrations. Inlet and outlet concentrations of constituents, contact times and results for each run are given below in Table I.

TABLE I

A. Inlet Concentrations

| Run | Temp. °C. | $O_2$ | $C_2H_4$ | HCl | TCTFE | $N_2$ |
|---|---|---|---|---|---|---|
| 1 | 485 | 12.89 | 32.33 | 13.72 | 15.45 | 25.61 |
| 2 | 475 | 12.12 | 32.09 | 14.96 | 15.25 | 25.88 |
| 3 | 466 | 11.40 | 32.82 | 15.64 | 14.79 | 25.35 |
| 4 | 461 | 11.04 | 32.77 | 14.39 | 15.54 | 26.26 |
| 5 | 451 | 11.04 | 32.73 | 14.84 | 15.73 | 25.66 |
| 6 | 445 | 11.28 | 32.98 | 14.58 | 15.58 | 25.58 |
| 7 | 440 | 11.22 | 32.97 | 14.78 | 15.30 | 25.73 |
| 8 | 435 | 11.32 | 33.25 | 14.61 | 14.99 | 25.83 |
| 9 | 425 | 11.86 | 32.70 | 14.58 | 15.22 | 25.64 |

B. Exit Compositions

| Run | $C_2H_4$ | TCTFE | $CO_2$ | CO | CTFE | VCM | EDC |
|---|---|---|---|---|---|---|---|
| 1 | 16.02 | 14.35 | 1.74 | .26 | 1.46 | 11.61 | 1.30 |
| 2 | 17.15 | 13.85 | 1.28 | .19 | 1.16 | 11.29 | 1.91 |
| 3 | 18.05 | 13.39 | 1.32 | .14 | .92 | 10.72 | 2.27 |
| 4 | 18.24 | 14.28 | 1.15 | .10 | .92 | 10.94 | 2.59 |
| 5 | 17.94 | 14.72 | 1.07 | .07 | .76 | 10.46 | 2.96 |
| 6 | 17.82 | 14.79 | 1.01 | .05 | .59 | 9.78 | 3.39 |
| 7 | 17.60 | 14.96 | .96 | — | .50 | 9.13 | 3.84 |
| 8 | 17.24 | 14.72 | .84 | .03 | .42 | 8.51 | 4.23 |
| 9 | 16.14 | 14.95 | .92 | — | .31 | 7.87 | 4.25 |

C. Results

| Run | Moles Eth. Consumed | Moles Eth. to Combustion | % Eth. Consumed by Combustion | % Conversion of Eth. | % Eth. Converted to EDC & VCM | Moles TCTFE Consumed | % Conversion TCTFE |
|---|---|---|---|---|---|---|---|
| 1 | 16.31 | 1.00 | 6.13 | 50.44 | 79.15 | 1.10 | 7.11 |
| 2 | 14.94 | 0.74 | 4.95 | 46.55 | 88.35 | 1.40 | 9.18 |
| 3 | 14.77 | 0.73 | 4.94 | 45.00 | 87.94 | 1.40 | 9.46 |
| 4 | 14.53 | 0.62 | 4.26 | 44.33 | 93.11 | 1.26 | 8.10 |
| 5 | 14.79 | 0.57 | 3.85 | 45.18 | 90.73 | 1.01 | 6.42 |
| 6 | 15.16 | 0.53 | 3.49 | 45.96 | 86.87 | 0.79 | 5.07 |
| 7 | 15.37 | 0.48 | 3.12 | 46.61 | 84.38 | 0.34 | 2.22 |
| 8 | 16.01 | 0.43 | 2.68 | 48.15 | 79.57 | 0.27 | 1.80 |
| 9 | 16.56 | 0.46 | 2.77 | 50.64 | 73.18 | 0.27 | 1.77 |

The headings of Table I are explained as follows:

1. Contact Time: Catalyst void space/inlet gas flow rate at reaction temperature, where catalyst void space is taken as 50% of catalyst bed volume (i.e., reactor volume occupied by the catalyst bed.)
2. Moles Eth. Consumed: moles ethylene in inlet stream-moles ethylene in outlet stream.
3. Moles Eth. to Combustion: ½ (moles $CO+CO_2$ in outlet stream).
4. % Eth. Consumed by Combustion: 100 (moles ethylene to combustion/moles ethylene consumed).
5. % Conversion of Eth.: 100 (moles ethylene consumed/moles ethylene in inlet stream).
6. % Eth. Converted to EDC and VCM: 100 (moles EDC+moles VCM in outlet/moles ethylene consumed).
7. Moles TCTFE Consumed: moles TCTFE in inlet stream/moles TCTFE in outlet stream.
8. % Conversion TCTFE: 100 (moles TCTFE consumed/moles TCTFE in inlet stream).

As is seen in the above table, Run 2, conducted at 475° C., gave the best results in producing a 9.18% conversion of TCTFE, wherein only 5% of ethylene was consumed by combustion and 88% of ethylene converted was converted to EDC and VCM.

EXAMPLE D

The catalyst prepared in Example A was used in a series of 8 runs wherein the catalyst weight was 3.5138 grams, total catalyst bed volume was 4.0 ml, and the flow rate of the inlet gas stream was 37.0 ml/min (STP). The average contact time in the runs was about 1.3 seconds. Nitrogen was used to normalize the inlet and outlet concentrations. Inlet and outlet concentrations, contact times, and results from each run are given below in Table II. The definition of the headings in Table II are the same as used in Table I.

TABLE II

A. Inlet Concentrations

| Run | Temp °C. | $O_2$ | $C_2H_4$ | HCl | TCTFE | $N_2$ |
|---|---|---|---|---|---|---|
| 1 | 487 | 6.72 | 21.35 | 18.51 | 18.64 | 34.78 |
| 2 | 479 | 7.26 | 21.08 | 18.11 | 17.93 | 35.62 |
| 3 | 474 | 6.71 | 20.22 | 20.19 | 17.72 | 35.16 |
| 4 | 465 | 7.24 | 19.54 | 23.04 | 16.77 | 33.41 |
| 5 | 456 | 6.76 | 19.34 | 21.46 | 17.08 | 35.36 |
| 6 | 450 | 6.58 | 19.18 | 22.26 | 16.62 | 35.36 |
| 7 | 442 | 6.64 | 18.76 | 21.97 | 17.04 | 35.59 |
| 8 | 435 | 6.88 | 19.16 | 21.28 | 16.49 | 36.19 |

B. Exit Concentrations

TABLE II-continued

| Run | C$_2$H$_4$ | TCTFE | CO$_2$ | CO | CTFE | VCM | EDC |
|---|---|---|---|---|---|---|---|
| 1 | 13.92 | 16.21 | .71 | 3.07 | 1.70 | 2.57 | 1.17 |
| 2 | 13.57 | 16.85 | .59 | 2.12 | 1.46 | 2.90 | 1.49 |
| 3 | 13.28 | 16.78 | .52 | 1.67 | 1.17 | 2.94 | 1.70 |
| 4 | 12.38 | 15.31 | .45 | 1.17 | .95 | 2.69 | 1.79 |
| 5 | 12.83 | 15.98 | .41 | .79 | .68 | 2.49 | 2.29 |
| 6 | 12.73 | 16.23 | .34 | .48 | .45 | 2.28 | 2.58 |
| 7 | 12.78 | 17.01 | .31 | 34 | .37 | 2.11 | 2.95 |
| 8 | 12.79 | 15.87 | .30 | .19 | .29 | 1.90 | 3.37 |

C. Results

| Run | Moles Eth. Consumed | Moles Eth. to Combustion | % Eth. Consumed by Combustion | % Conversion of Eth. | % Eth. Converted to EDC & VCM | Moles TCTFE Consumed | % Conversion TCTFE |
|---|---|---|---|---|---|---|---|
| 1 | 7.43 | 1.89 | 25.43 | 34.80 | 50.33 | 2.43 | 13.03 |
| 2 | 7.51 | 1.35 | 17.97 | 35.62 | 58.45 | 1.08 | 6.02 |
| 3 | 6.94 | 1.09 | 15.70 | 34.32 | 66.85 | 0.94 | 5.30 |
| 4 | 7.16 | 0.81 | 11.31 | 36.64 | 62.56 | 1.46 | 8.70 |
| 5 | 6.51 | 0.60 | 9.21 | 33.66 | 73.42 | 1.10 | 6.44 |
| 6 | 6.45 | 0.41 | 6.35 | 33.62 | 75.34 | 0.39 | 2.34 |
| 7 | 5.98 | 0.32 | 5.35 | 31.87 | 84.61 | 0.03 | 0.17 |
| 8 | 6.37 | 0.25 | 3.92 | 33.24 | 82.73 | 0.62 | 3.75 |

As is seen in Table II, the catalyst prepared from molecular sieve 5A produced acceptable conversions of TCTFE. However, the percent combustion of ethylene was in general, higher. This illustrates that although the catalyst, prepared from a 5 angstrom pore size diameter molecular sieve, gave acceptable results in terms of TCTFE conversion and ethylene conversion, it is considered that smaller pore sizes would probably lead to unacceptably high combustion yields of ethylene.

We claim:

1. In a process for converting 1,1,2-trichloro-1,2,2-trifluoroethane to chlorotrifluoroethylene, the improvement which comprises passing said trichlorotrifluoroethane in a mixture of oxygen, hydrogen chloride and ethylene in the vapor phase over a catalyst consisting essentially of a mixture of copper chloride and an alkali metal chloride salt occluded in a molecular sieve, having an average pore size diameter in the range of about 5 to 11 angstroms, at a temperature in the range of about 350° C. to 525° C., for a contact time of about 0.1 to 30 seconds.

2. The process of claim 1 wherein the molar ratio of 1,1,2-trichloro-1,2,2-trifluoroethane/ethylene/HCl/oxygen is about 2:4:4:1.

3. The process of claim 1 wherein the process is conducted at a temperature of about 450° C. to 500° C.

4. The process of claim 1 wherein the contact time is about 1 to 3 seconds.

5. The process of claim 1 wherein the alkali metal chloride is potassium chloride.

6. The process of claim 1 wherein the average pore size diameter of the molecular sieve is about 10 angstroms.

7. The process of claim 1 wherein the weight ratio of the molecular sieve to the mixture of copper chloride and alkali metal chloride is about 6 parts molecular sieve to 4 parts by weight of the mixture.

8. The process of claim 1 wherein the molecular ratio of copper chloride to alkali metal chloride salt is about 1:1.

9. The process of claim 1 wherein the mixture of copper chloride and alkali metal chloride further contains rare earth chloride, or mixtures thereof.

10. The process of claim 9 wherein the molar ratio of copper chloride/alkali metal chloride/rare earth chloride is about 7:4:1, respectively.

11. The process of claim 1 wherein the mixture of copper chloride and alkali metal chloride is a eutectic mixture.

* * * * *